(12) United States Patent
Eidenschink

(10) Patent No.: US 7,367,967 B2
(45) Date of Patent: May 6, 2008

(54) CATHETER WITH SHEATHED HYPOTUBE

(75) Inventor: Tracee Eidenschink, Wayzata, ME (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 587 days.

(21) Appl. No.: 10/664,132

(22) Filed: Sep. 17, 2003

(65) Prior Publication Data

US 2005/0059959 A1    Mar. 17, 2005

(51) Int. Cl.
A61M 25/00 (2006.01)

(52) U.S. Cl. .................................................. 604/523

(58) Field of Classification Search ............ 604/96.01, 604/103.9, 264, 523–526, 915, 921; 606/192, 606/194

See application file for complete search history.

(56) References Cited

U.S. PATENT DOCUMENTS

| | | | |
|---|---|---|---|
| 4,251,305 A | 2/1981 | Becker et al. | 156/86 |
| 4,636,272 A | 1/1987 | Riggs | 156/158 |
| 4,943,278 A | 7/1990 | Euteneuer et al. | 604/96 |
| 4,964,409 A | 10/1990 | Tremulis | 128/657 |
| 5,046,497 A | 9/1991 | Millar | 128/637 |
| 5,047,045 A | 9/1991 | Arney et al. | 606/194 |
| 5,100,381 A | 3/1992 | Burns | 604/96 |
| 5,154,725 A | 10/1992 | Leopold | 606/194 |
| 5,156,594 A | 10/1992 | Keith | 604/96 |
| 5,261,879 A | 11/1993 | Brill | 604/96 |
| 5,279,562 A | 1/1994 | Sirhan et al. | 604/96 |
| 5,281,203 A | 1/1994 | Ressemann | 604/164 |
| 5,295,961 A | 3/1994 | Niederhauser et al. | 604/96 |
| 5,304,134 A | 4/1994 | Kraus et al. | 604/96 |
| 5,306,247 A | 4/1994 | Pfenninger | 604/96 |
| 5,346,505 A | 9/1994 | Leopold | 606/194 |
| 5,370,616 A | 12/1994 | Keith et al. | 604/102 |
| 5,370,655 A | 12/1994 | Burns | 606/194 |
| 5,383,853 A | 1/1995 | Jung et al. | 604/96 |
| 5,387,193 A | 2/1995 | Miraki | 604/96 |
| 5,395,334 A | 3/1995 | Keith et al. | 604/102 |
| 5,397,306 A | 3/1995 | Nobuyoshi et al. | 604/96 |
| 5,439,447 A | 8/1995 | Miraki | 604/96 |
| 5,480,383 A | 1/1996 | Bagaoisan et al. | 604/96 |
| 5,490,837 A | 2/1996 | Blaeser et al. | 604/96 |
| 5,522,818 A | 6/1996 | Keith et al. | 604/102 |

(Continued)

FOREIGN PATENT DOCUMENTS

WO    01/89621 A    5/2001

(Continued)

*Primary Examiner*—Nicholas D. Lucchesi
*Assistant Examiner*—Christopher D Koharski
(74) *Attorney, Agent, or Firm*—Vidas, Arrett & Steinkraus

(57) ABSTRACT

A catheter assembly and method for constructing same comprises the engagement of a substantially hollow proximal tubular member, which is at least partially coated with at least one polymeric material, to a substantially distal outer tubular member. The proximal tubular member and the distal outer tubular member define at least one continuous central lumen therethrough. At least a portion of the distal outer tubular member is disposed about at least a portion of an inner tubular member. A portion of the inner tubular member is engaged to a portion of the proximal tubular member. A portion of the inner tubular member is engaged to a portion of the end region of the distal outer member. An end region of the proximal tubular member extends distally into the distal outer tubular member adjacent to the inner tubular member.

23 Claims, 6 Drawing Sheets

U.S. PATENT DOCUMENTS

| | | |
|---|---|---|
| 5,549,552 A | 8/1996 | Peters et al. .................. 604/96 |
| 5,549,556 A | 8/1996 | Ndondo-Lay et al. ...... 604/102 |
| 5,567,203 A | 10/1996 | Euteneuer et al. ............ 604/96 |
| 5,702,439 A * | 12/1997 | Keith et al. ............... 604/96.01 |
| 5,976,107 A | 11/1999 | Mertens et al. ............... 604/96 |
| 5,980,484 A | 11/1999 | Ressemann et al. .......... 604/96 |
| 6,102,890 A | 8/2000 | Stivland et al. ............... 604/96 |
| 6,129,708 A | 10/2000 | Enger .................... 604/103.04 |
| 6,179,810 B1 | 1/2001 | Wantink et al. ............... 604/96 |
| 6,193,686 B1 | 2/2001 | Estrada et al. ......... 604/103.09 |
| 6,238,376 B1 | 5/2001 | Peterson .................... 604/264 |
| 6,273,879 B1 | 8/2001 | Keith et al. ................. 604/523 |
| 6,319,229 B1 | 11/2001 | Kim et al. ................... 604/103 |
| 6,361,529 B1 | 3/2002 | Goodin et al. ............. 604/524 |
| 6,387,075 B1 | 5/2002 | Stivland et al. ............... 604/96 |
| 6,398,799 B2 | 6/2002 | Kramer ...................... 606/194 |
| 6,458,099 B2 | 10/2002 | Dutta et al. ............ 604/103.04 |
| 6,458,867 B1 | 10/2002 | Wang et al. ................. 523/105 |
| 6,461,347 B1 | 10/2002 | Von Hoffmann ............ 604/508 |
| 6,475,187 B1 | 11/2002 | Gerberding ............ 604/102.02 |
| 6,488,655 B1 | 12/2002 | Wantink et al. ........ 604/103.09 |
| 6,503,223 B1 | 1/2003 | Sekido et al. ............ 604/96.01 |
| 6,520,951 B1 | 2/2003 | Carrillo, Jr. et al. ........ 604/516 |
| 6,548,010 B1 | 4/2003 | Stivland et al. ............. 264/482 |
| 6,558,401 B1 | 5/2003 | Azizi ......................... 606/159 |
| 6,575,958 B1 | 6/2003 | Happ et al. ................. 604/525 |
| 6,589,207 B1 | 7/2003 | El-Nounou ............ 604/103.04 |
| 6,605,057 B2 | 8/2003 | Fitzmaurice et al. ... 604/102.02 |
| 6,605,062 B1 | 8/2003 | Hurley et al. .......... 604/164.13 |
| 6,613,066 B1 | 9/2003 | Fukaya et al. ............. 606/192 |
| 2002/0038103 A1 | 3/2002 | Estrada et al. ......... 604/103.09 |

FOREIGN PATENT DOCUMENTS

WO     03/037418 A     5/2003

* cited by examiner

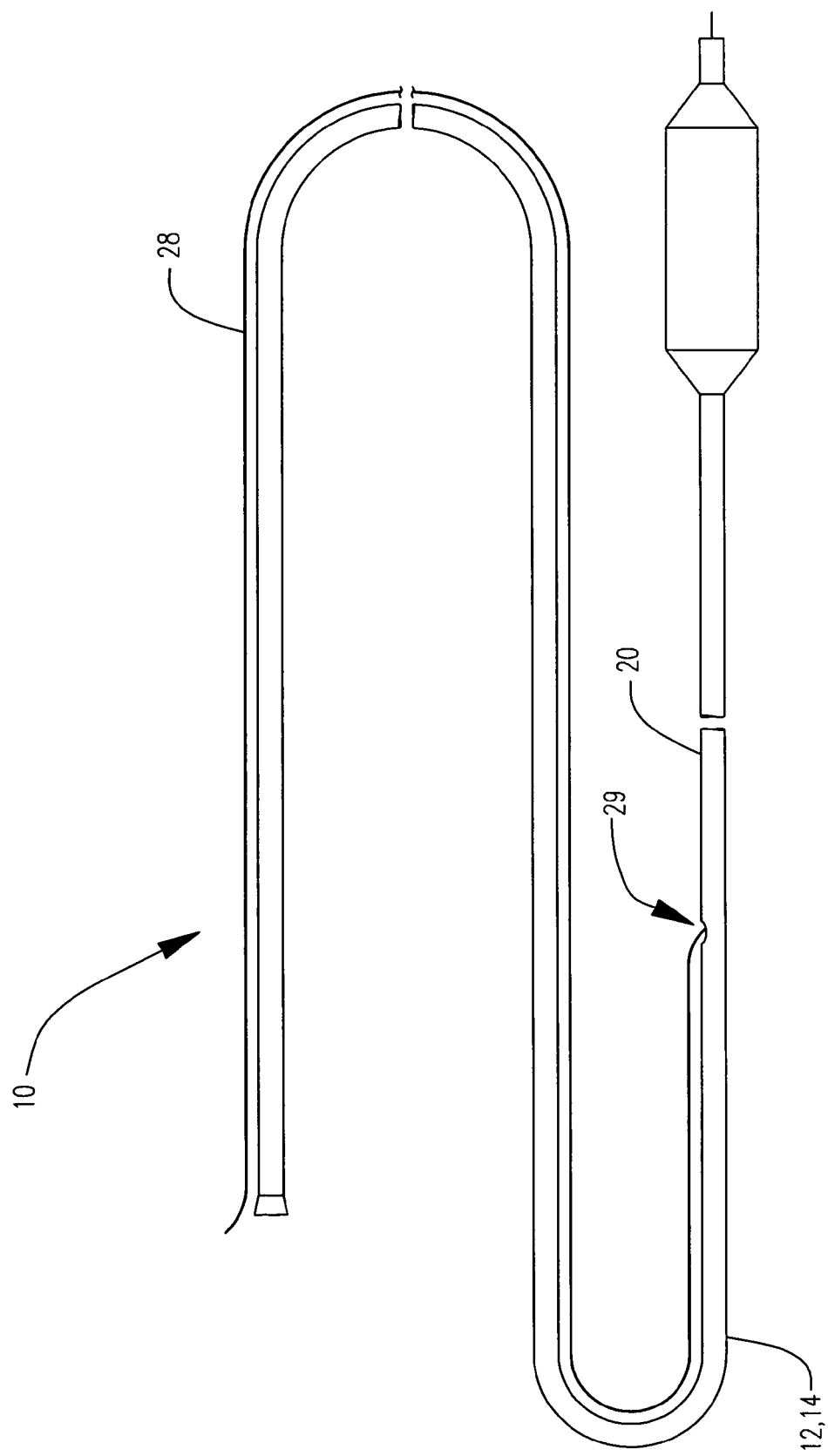

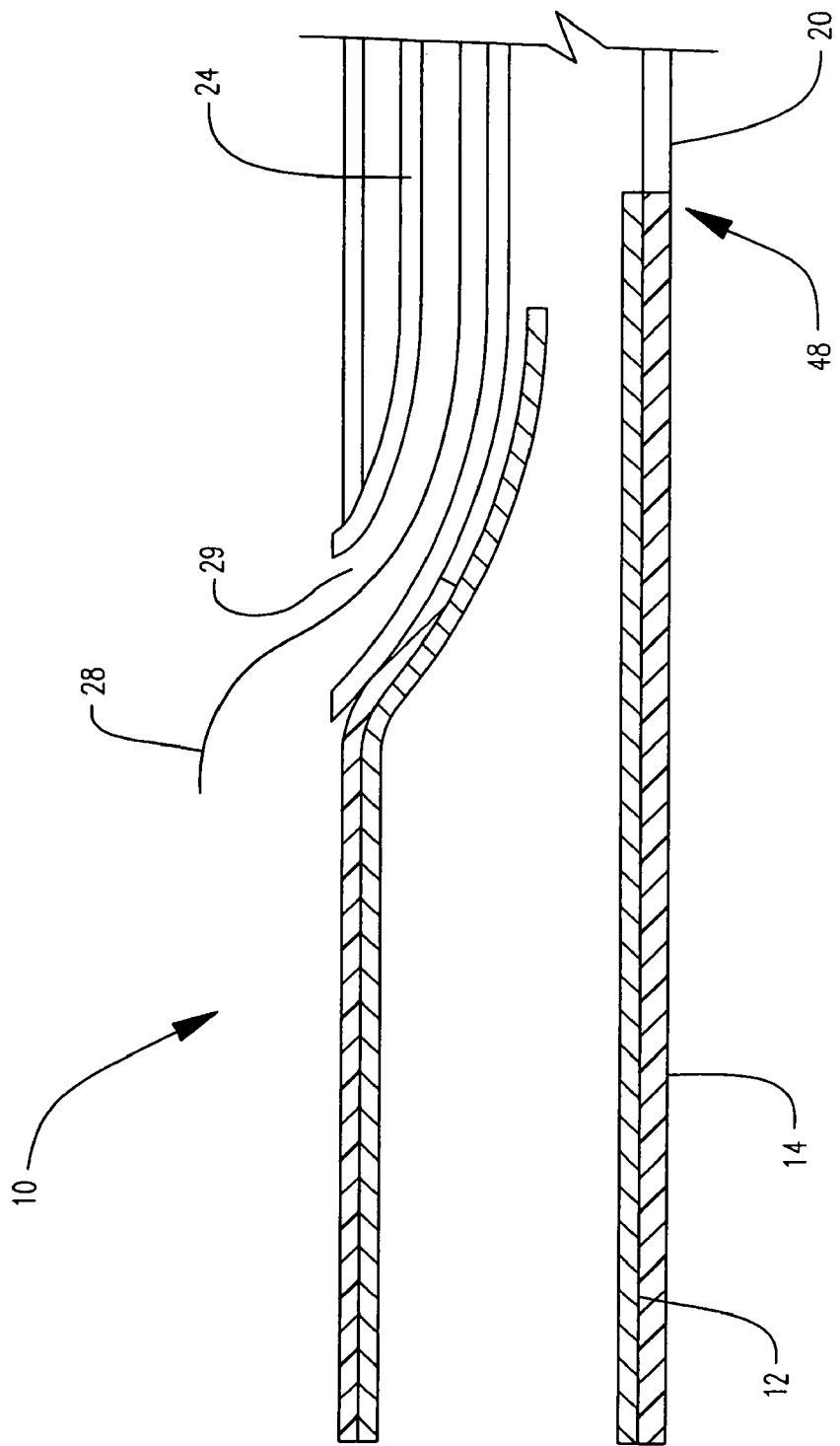

CATHETER WITH SHEATHED HYPOTUBE

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention is directed to a variety of embodiments. At least one embodiment of the invention is directed to the field of intravascular medical devices, and more particularly to the field of catheters such as angioplasty, neurological and guide catheters, among others, which may be used in various medical procedures such as percutaneous transluminal angioplasty (PTA), percutaneous transluminal coronary angioplasty (PTCA) as well as in procedures involving the placement of medicines and medical devices within the body.

Some embodiments of the invention are directed to all forms of catheters which may be advanced through a body lumen or vessel. Some examples of catheters are over-the-wire (OTW) catheters, such as are described in U.S. Pat. No. 5,047,045; single-operator-exchange (SOE) balloon catheters, such as are described in U.S. Pat. No. 5,156,594 and U.S. Pat. No. 5,549,552. Other examples of catheters which may incorporate the unique features of the present invention include rapid-exchange style balloon catheters, MONO-RAIL® dilatation catheters available from SciMed Life Systems, Inc. of Maple Grove, Minn., etc.

2. Description of the Related Art

Intravascular diseases are commonly treated by relatively non-invasive techniques such as PTA and PTCA. These angioplasty techniques typically involve the use of a balloon catheter. In these procedures, a balloon catheter is advanced through the vasculature of a patient such that the balloon is positioned proximate a constriction in a diseased vessel. The balloon is then inflated and the constriction in the vessel is opened. In other uses a catheter may be used to deliver an endoprosthesis such as a stent, graft, stent-graft, filter or other implantable or optionally implantable device or devices herein after collectively referred to as a stent or stents. Where a stent is to be delivered into a body lumen the catheter may include one or more inflatable portions or balloons. Typically, the stent is retained in the predelivery state about the catheter shaft, or a portion thereof such as a balloon, by crimping and/or through the use of a retaining mechanism such as sleeve, sheath or sock.

Balloons and balloon catheters may be particularly useful for the delivery of stents. Stents and catheters used in their delivery are commonly used and as such their structure and function are well known.

Many rapid exchange catheters, including some types of balloon catheters, comprise a proximal portion, often include a hypotube which can be constructed from a variety of non-thermoplastic and/or metallic material(s). This hypotube is joined to a distal outer shaft portion of the catheter at a port area by using a mid-shaft tube that connects the catheter sections together. Typically, the outer shaft is at least partially constructed of a polymer substance. The port area is the area of the catheter where the proximal guide wire exits the catheter assembly such as is shown in the PRIOR ART drawing labeled FIG. 1. A core wire or other member can aid in support of the mid-shaft area.

A goal of the present invention is to provide a more simplified and efficient catheter assembly design that avoids the necessity of a mid-shaft tube to link the distal outer to the hypotube, as well as to avoid the use of a core wire.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

As indicated above, the present invention may be embodied in a variety of forms. In at least one embodiment the invention is directed to a catheter assembly which avoids the use of a mid-shaft tube by directly engaging the proximal shaft portion or hypotube directly to the distal outer by providing at least a distal portion of the hypotube with a polymeric sheath which may be bonded directly to the distal outer. Where a guide wire port is required, a portion of the sheath is bonded to the distal outer and a portion is bonded to the inner shaft which defines the proximal guide wire port.

In some embodiments a portion of the hypotube extends distally a predetermined length beyond the guide wire port. In this manner the hypotube supports the mid-shaft region of the catheter without the need of an additional mind-shaft tube or core wire support.

In at least one embodiment the hypotube sheath comprises one or more materials such as polyesters; polyurethanes; polyamides; polyolefins including polyethylene and polypropylene; and any copolymers thereof. Some more specific examples of suitable materials include, but are not limited to: nylon; polyester elastomer; polyether/block polyamide, such as Pebax, Hytrel, and/or Arnitel; polyamid such as Grilamid; flouro-polymer, such as Kynar; polyether ether ketone (PEEK); polyethylene (PE); polyurethane; polyolefin copolymer (POC); tetrafluoroethylenes, such as polytetrafluoroethylene (PTFE); etc.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 5 is a side elevational view of a balloon dilatation catheter with the embodiment of FIG. 2.

FIG. 6 is a cross-sectional view of the embodiment shown in FIG. 2 with a butt-weld engagement between the outer shaft and the coating.

DETAILED DESCRIPTION OF THE INVENTION

Figure 1:
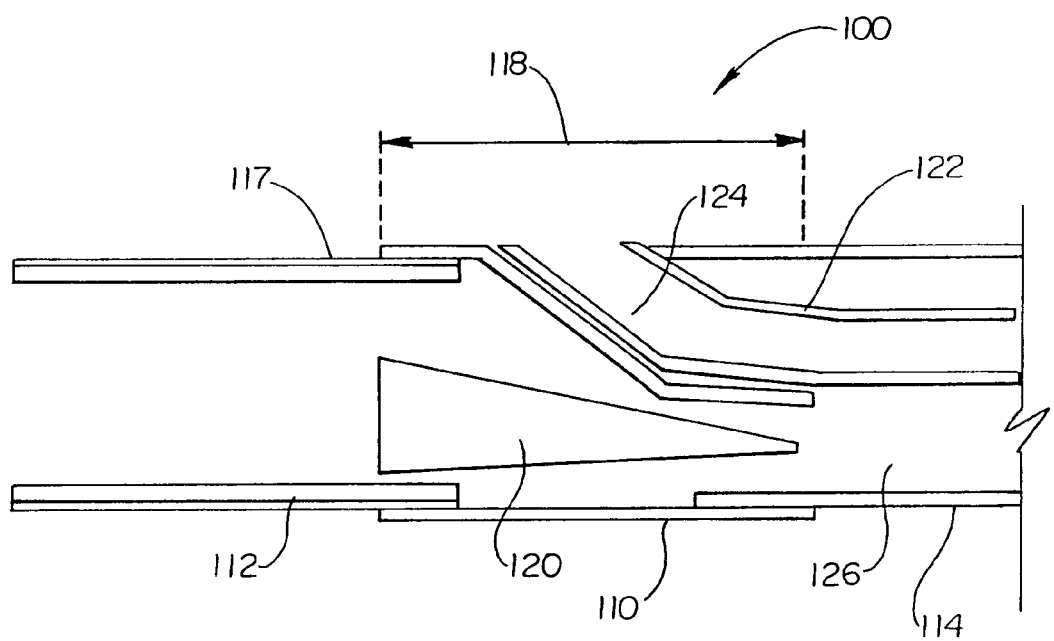
FIG. 1 is a longitudinal side view of a mid-shaft region of a catheter assembly which is representative of a PRIOR ART assembly.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above, FIG. 1 shows a longitudinal cross-section of a PRIOR ART catheter assembly 100, which employs a mid-shaft tube 110 to connect the proximal shaft or hypotube 112 and distal outer 114. The mid-shaft tube 110 is welded, bonded or otherwise engaged to the proximal shaft 112 via a polymeric coating 117. The mid-shaft tube 110 supports the inner shaft 122 which defines a proximal guide wire lumen 124. A core wire 120 extends through an inflation lumen 126 defined by the hypotube 112 to provide further support and reinforcement of the port bond 118 of the mid-shaft region shown.

Figure 2:
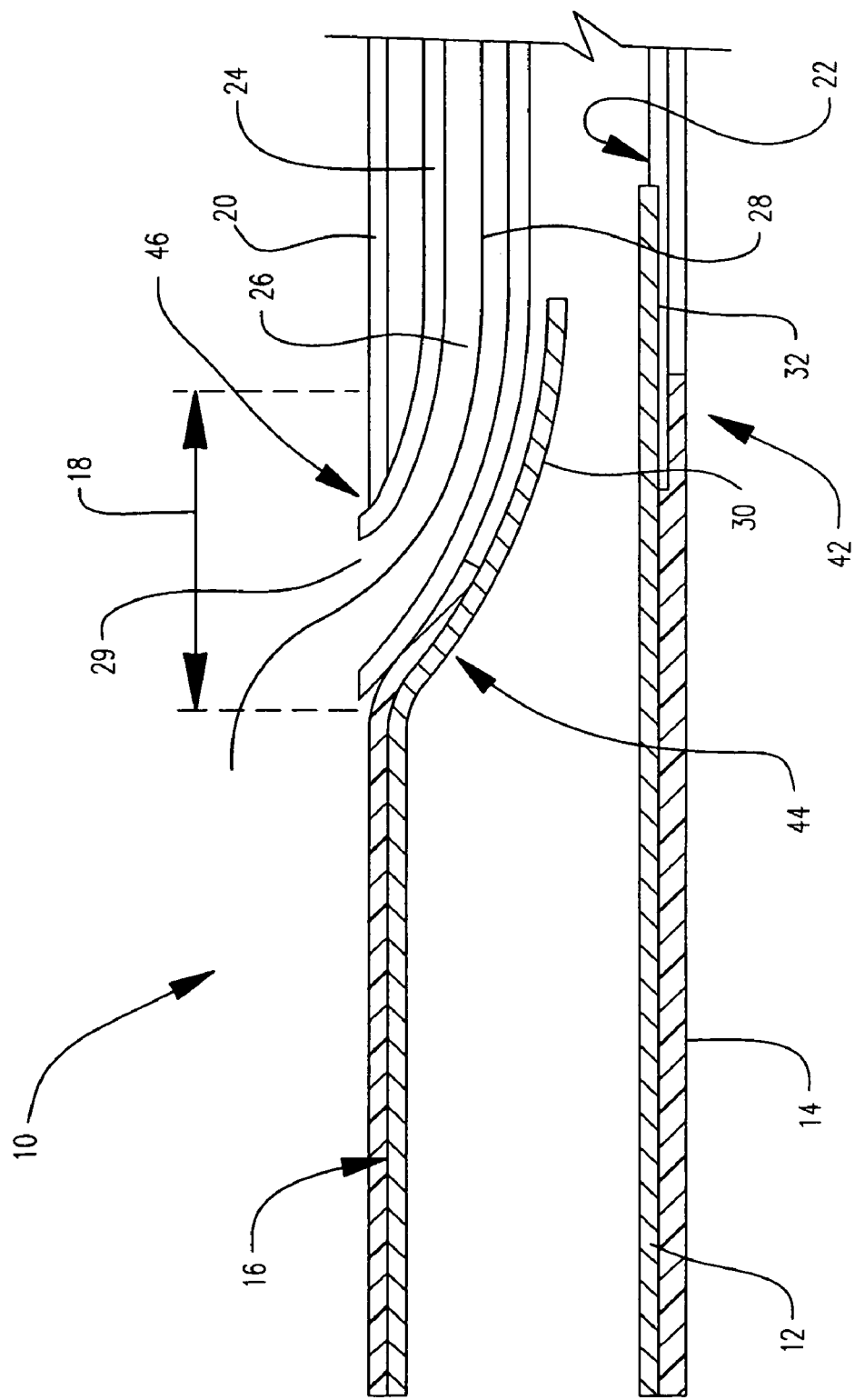
FIG. 2 is a longitudinal side view of an embodiment of the invention.

In at least one embodiment of the present invention a catheter assembly, indicated generally at 10 in FIG. 2, is assembled without employing a mid-shaft tube and/or a core wire such as previously described. The catheter assembly may be a balloon catheter 10, as illustrated in FIG. 5.

In the embodiment shown in FIG. 2 a proximal shaft or hypotube 12 includes a sheath or coating 14 of one or more polymeric materials such as polyesters; polyurethanes; polyamides; polyolefins including polyethylene and polypropylene; and any copolymers thereof. Some more specific examples of suitable materials include, but are not limited to: nylon; polyester elastomer; polyether/block polyamide, such as Pebax, Hytrel, and/or Arnitel; polyamid such as Grilamid; flouro-polymer, such as Kynar; polyether ether ketone (PEEK); polyethylene (PE); polyurethane; polyolefin copolymer (POC); tetrafluoroethylenes, such as polytetrafluoroethylene (PTFE); etc.

Coating 14 may be applied to the external surface 16 of at least a portion of the hypotube 12, or may be a tubular member of material disposed thereabout. In some embodiments the hypotube 12 is at least partially constructed from one or more non-thermoplastic polymers and/or metal. In the embodiment shown, at least one side, of the distal end, of the hypotube 12 is engaged to the interior surface 22 of the distal outer shaft 20, in an overlapping configuration. The coating 14 is welded or otherwise bonded to the distal outer shaft 20. The coating 14 may form a continuous polymeric layer of material with the distal outer shaft 20. In some embodiments the distal outer shaft 20 radially overlaps at least a portion of the coating 14, or alternatively the coating 14 radially overlaps at least a portion of the distal outer shaft 20. In at least one embodiment an end-to-end (butt-weld) engagement configuration (48) is provided between the outer shaft 20 and the coating 14, as shown in FIG. 6.

As illustrated in FIG. 2, the catheter assembly 10 has three engagement regions 42, 44 and 46. The engagement of the hypotube 12 and the distal outer shaft 20 forms a first engagement region 42. The engagement of the hypotube 12 and the inner shaft 24 forms a second engagement region 44. The engagement of the inner shaft 24 and the outer shaft 20 forms a third engagement region 46.

Depending on the material selected for coating 14, the coating 14 may act as a lubricious polymer shrinkable tube that is suitable for thermal welding of polymers of the adjacent structures.

In at least one embodiment the hypotube 12 is at least partially constructed of one or more metals such as stainless steel, titanium, nickel, and/or alloys thereof. The distal end of the hypotube 12 may extend beyond the region where the distal outer is bonded to the hypotube 12 via coating 14 to provide greater radial support to the port bond 18 and push strength to the catheter 10. Because only a portion of the hypotube 12 is bonded to the distal outer shaft 20 as previously described, flexibility of the port bond region is enhanced.

In addition to allowing the distal outer shaft 20 to be directly engaged to the hypotube 12, the coating 14 similarly provides for direct engagement of the inner shaft 24 to at least one side of the hypotube 12 as well. As is shown in FIG. 2 the inner shaft 24 defines a lumen 26 through which a guide wire 28 is passed. Inner shaft 24 also defines the port 29 where the guide wire 28 exits the catheter 10.

Due to the presence of the hypotube 12 underlying the port bond 18 of the catheter 10, the coated hypotube 12 may be directly engaged to the distal outer tube 20 by welding, bonding, physical engagement, or other engagement method(s) without the need of a mandrel or other support member.

Figure 3:
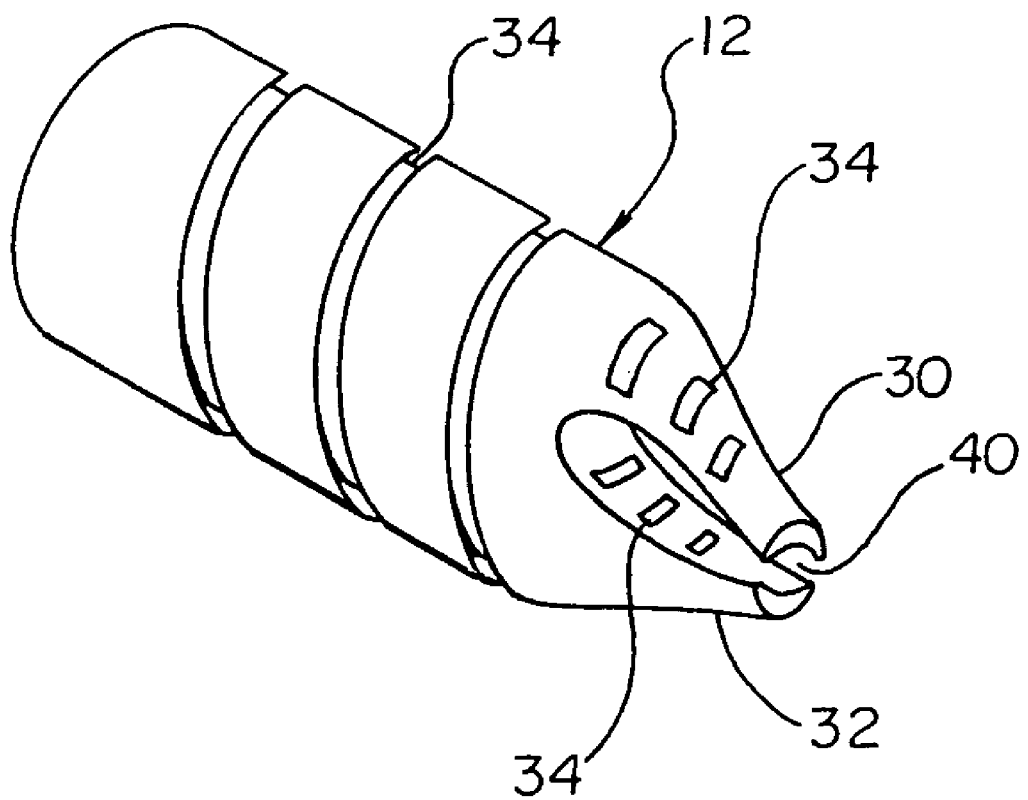
FIG. 3 is a perspective side view of a hypotube configuration suitable for use in the embodiment shown in FIG. 2.

In at least one embodiment the hypotube 12 is provided with sides 30 and 32 which are of equal or unequal length. Where one side 32 of the hypotube 12 is longer than other side 30, the longer side 32 acts in place of the core wire to provide strain relief. As a result, the use of a core wire, such as has been previously described, is avoided in the present invention. As is shown in the embodiment depicted in FIG. 3, at least a portion of the hypotube 12 may be provided with one or more indentations, spaces or cuts 34 in a spiral, helical or other geometric configuration. By providing the hypotube 12 with a spiral cut 34 strain relief as well as flexibility is further enhanced.

Figure 4:
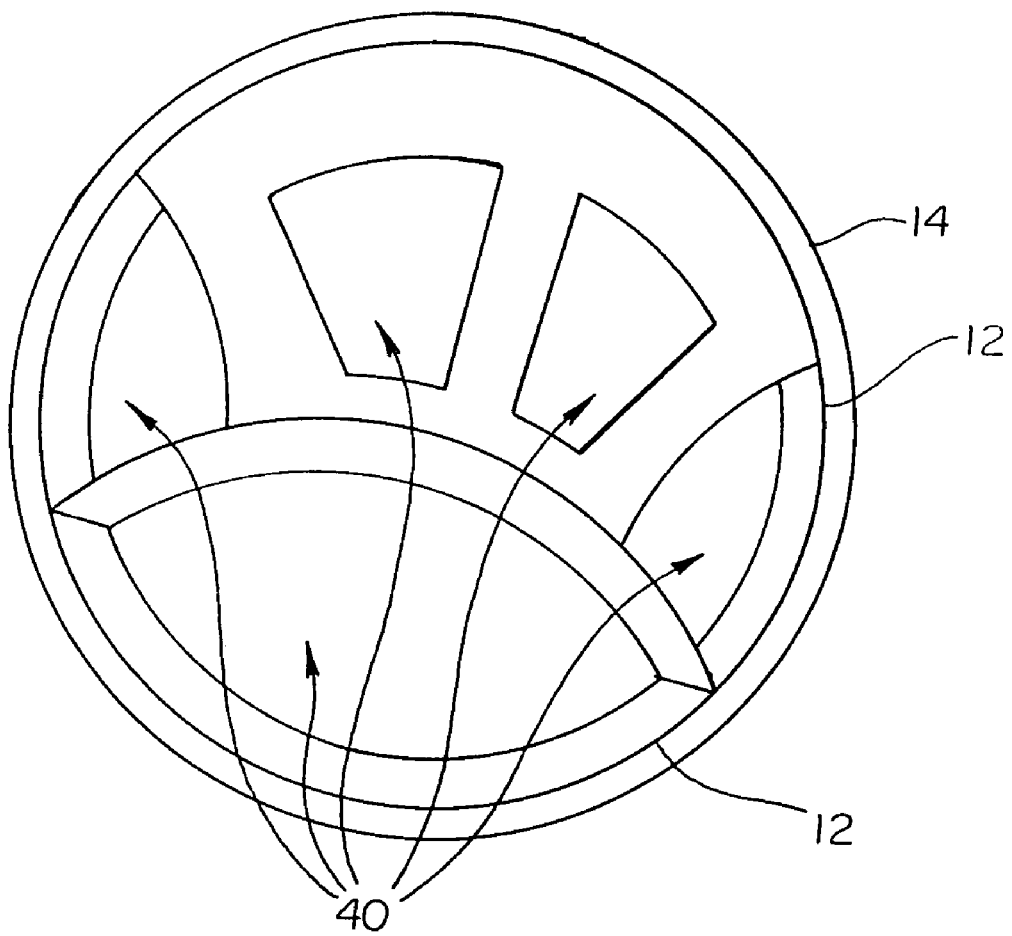
FIG. 4 is a cross-sectional view of the embodiment shown in FIG. 2

In addition to the above, it is also noted that as the distal end of the hypotube 12 advances through the port bond 18 of the catheter the hypotube 12 is deformed or otherwise provided with a more elliptical cross-sectional shape, such as is shown in FIG. 4. The unique curvature of the hypotube 12 where it extends through the port bond allows the hypotube 12 to act as a supportive bridge or keystone in an arch to provide significant compression resistance to prevent collapse of the inflation lumen(s) 40.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A catheter assembly comprising:
a substantially hollow proximal tubular member, at least a portion of the proximal tubular member having a coating of at least one thermoplastic polymer thereabout, the proximal tubular member having an end region, at least the end region having the coating of at least one thermoplastic polymer;
a substantially distal outer tubular member, the distal outer tubular member having an end region, a first portion of the end region of the distal outer tubular member being engaged to a first portion of the coating on a first portion of the end region of the proximal tubular member to define a first engagement region, the first engagement region comprising the first portion of the end region of the distal outer tubular member radially overlapping the first portion of the end region of the proximal tubular member, a first portion of the coating and the first portion of the end region of the distal outer tubular member being bonded together, the proximal tubular member and the distal outer tubular member defining at least one continuous central lumen therethrough; and
a substantially hollow inner tubular member, at least a portion of the distal outer tubular member disposed about at least a portion of the inner tubular member, a first portion of the inner tubular member engaged to the coating on a second portion of the end region of the proximal tubular member to define a second engagement region, a second portion of the inner tubular member engaged to a second portion of the end region of the distal outer member to define a third engagement region, the end region of the proximal tubular member extending distally into the distal outer tubular member adjacent to the at least a portion of the inner tubular member.

2. The catheter assembly of claim 1 wherein the catheter assembly is a balloon catheter.

3. The catheter assembly of claim 1 wherein the catheter assembly is a monorail catheter or a rapid-exchange catheter.

4. The catheter assembly of claim 1 wherein the proximal tubular member is at least partially constructed from metal.

5. The catheter assembly of claim 1 wherein the coating is selected from at least one member of the group consisting of: nylon, polyester elastomer, polyether/block polyamide, polyamide, flouro-polymer, PEEK, PE, polyurethane, POC, PTFE and any combination thereof.

6. The catheter of claim 1 wherein the proximal tubular member is a hypotube.

7. The catheter of claim 1 wherein the distal outer tubular member is at least partially constructed from at least one polymeric material.

8. The catheter of claim 1 wherein the distal outer tubular member is at least partially constructed from at least one member of the group consisting of: nylon, polyester elastomer, polyether/block polyamide, polyamide, flouro-polymer, PEEK, PE, polyurethane, POC, PTFE and any combination thereof.

9. The catheter assembly of claim 1 wherein a first portion of the coating and the first portion of the end region of the distal outer tubular member are bonded together in a continuous layer.

10. The catheter assembly of claim 1 wherein the inner member defines a guide wire lumen.

11. The catheter assembly of claim 1 wherein the inner member is at least partially constructed from at least one member of the group consisting of: nylon, polyester elastomer, polyether/block polyamide, polyamide, flouro-polymer, PEEK, PE, polyurethane, POC, PTFE and any combination thereof.

12. The catheter assembly of claim 1 wherein the proximal tubular member has a substantially elliptical cross-sectional shape.

13. A catheter assembly comprising:
a substantially hollow proximal tubular member, at least a portion of the proximal tubular member having a coating of at least one thermoplastic polymer thereabout, the proximal tubular member having an end region, at least the end region having the coating of at least one thermoplastic polymer;
a substantially distal outer tubular member, the distal outer tubular member having an end region, a first portion of the end region of the distal outer tubular member being engaged to a first portion of the coating on a first portion of the end region of the proximal tubular member to define a first engagement region, the first engagement region comprising the first portion of the end region of the distal outer tubular member radially overlapping the first portion of the end region of the proximal tubular member, a first portion of the coating and the first portion of the end region of the distal outer tubular member are welded together in a butt-weld configuration, the proximal tubular member and the distal outer tubular member defining at least one continuous central lumen therethrough; and
a substantially hollow inner tubular member, at least a portion of the distal outer tubular member disposed about at least a portion of the inner tubular member, a first portion of the inner tubular member engaged to the coating on a second portion of the end region of the proximal tubular member to define a second engagement region, a second portion of the inner tubular member engaged to a second portion of the end region of the distal outer member to define a third engagement region, the end region of the proximal tubular member extending distally into the distal outer tubular member adjacent to the at least a portion of the inner tubular member.

14. The catheter assembly of claim 13 wherein the catheter assembly is a balloon catheter.

15. The catheter assembly of claim 13 wherein the catheter assembly is a monorail catheter or a rapid-exchange catheter.

16. The catheter assembly of claim 13 wherein the proximal tubular member is at least partially constructed from metal.

17. The catheter assembly of claim 13 wherein the coating is selected from at least one member of the group consisting of: nylon, polyester elastomer, polyether/block polyamide, polyamide, flouro-polymer, PEEK, PE, polyurethane, POC, PTFE and any combination thereof.

18. The catheter of claim 13 wherein the proximal tubular member is a hypotube.

19. The catheter of claim 13 wherein the distal outer tubular member is at least partially constructed from at least one polymeric material.

20. The catheter of claim 13 wherein the distal outer tubular member is at least partially constructed from at least one member of the group consisting of: nylon, polyester elastomer, polyether/block polyamide, polyamide, flouro-polymer, PEEK, PE, polyurethane, POC, PTFE and any combination thereof.

21. The catheter assembly of claim 13 wherein the inner member defines a guide wire lumen.

22. The catheter assembly of claim 13 wherein the inner member is at least partially constructed from at least one member of the group consisting of: nylon, polyester elastomer, polyether/block polyamide, polyamide, flouro-polymer, PEEK, PE, polyurethane, POC, PTFE and any combination thereof.

23. The catheter assembly of claim 13 wherein the proximal tubular member has a substantially elliptical cross-sectional shape.

* * * * *